(12) United States Patent
Kazuhiko et al.

(10) Patent No.: US 12,102,742 B2
(45) Date of Patent: Oct. 1, 2024

(54) BLOOD PROCESSING FILTER

(71) Applicant: JMS Co., Ltd., Hiroshima (JP)

(72) Inventors: Nakamura Kazuhiko, Tokyo (JP); Yokomizo Tomohisa, Tokyo (JP)

(73) Assignee: JMS CO., LTD., Hiroshima (JP)

( * ) Notice: Subject to any disclaimer, the term of this patent is extended or adjusted under 35 U.S.C. 154(b) by 369 days.

(21) Appl. No.: 17/624,681

(22) PCT Filed: Jul. 10, 2020

(86) PCT No.: PCT/JP2020/026962
§ 371 (c)(1),
(2) Date: Jan. 4, 2022

(87) PCT Pub. No.: WO2021/006331
PCT Pub. Date: Jan. 14, 2021

(65) Prior Publication Data
US 2022/0257840 A1  Aug. 18, 2022

(30) Foreign Application Priority Data

Jul. 11, 2019 (JP) ................................ 2019-129435

(51) Int. Cl.
*A61M 1/02* (2006.01)
(52) U.S. Cl.
CPC ... *A61M 1/0218* (2014.02); *A61M 2202/0439* (2013.01)
(58) Field of Classification Search
None
See application file for complete search history.

(56) References Cited

U.S. PATENT DOCUMENTS

| 4,879,040 A | 11/1989 | Prince et al. |
| 4,994,188 A | 2/1991 | Prince |

(Continued)

FOREIGN PATENT DOCUMENTS

| CN | 1209758 | 3/1999 |
| CN | 102039062 | 5/2011 |

(Continued)

OTHER PUBLICATIONS

International Preliminary Report on Patentability received in International Application No. PCT/JP2020/026962, dated Jan. 11, 2022.

(Continued)

*Primary Examiner* — Jonathan M Peo
(74) *Attorney, Agent, or Firm* — GREENBLUM & BERNSTEIN, P.L.C.

(57) ABSTRACT

A blood processing filter, which may be used for white blood cell removal, includes a flexible container having an inlet and an outlet for blood. A filter medium disposed between the inlet and the outlet, and a flow passage-securing member disposed between the filter medium and the outlet. The filter medium includes a filter layer X1 including a filter component unit A1, and a filter layer Y including a filter component unit B. The filter layer X1 is disposed between the filter layer Y and the flow passage-securing member. Ventilation resistances of the filter component unit A1 and unit B are 5.0 Pa·s/m² or more and less than 9.0 Pa·s/m² and 9.0 Pa·s/m² or more, respectively. Ventilation resistances of the filter layer X1 and the filter medium are 4.0 kPa·s/m or more and 20.0 kPa·s/m or less and 55.0 kPa·s/m or more and less than 75.0 kPa·s/m, respectively.

4 Claims, 1 Drawing Sheet

(56) References Cited

U.S. PATENT DOCUMENTS

| | | | |
|---|---|---|---|
| 5,069,792 A | 12/1991 | Prince et al. | |
| 5,695,489 A | 12/1997 | Japuntich | |
| 7,641,794 B2 * | 1/2010 | Oka | A61M 1/3633 210/488 |
| 2002/0033367 A1 | 3/2002 | Prince et al. | |
| 2004/0149657 A1 * | 8/2004 | Yokomizo | A61M 1/3633 210/741 |
| 2004/0251195 A1 | 12/2004 | Oka et al. | |
| 2005/0133439 A1 | 6/2005 | Blickhan | |
| 2011/0031191 A1 | 2/2011 | Fukuda et al. | |
| 2012/0067810 A1 | 3/2012 | Yokomzo et al. | |
| 2014/0144832 A1 | 5/2014 | Yokomizo et al. | |
| 2014/0165517 A1 | 6/2014 | Hara et al. | |
| 2014/0299556 A1 | 10/2014 | Zambianchi et al. | |
| 2015/0265756 A1 | 9/2015 | Yokomizo | |
| 2015/0265954 A1 | 9/2015 | Lynn et al. | |
| 2016/0129176 A1 | 5/2016 | Kanaki et al. | |
| 2016/0235904 A1 * | 8/2016 | Yokomizo | A61M 1/1631 |
| 2017/0112982 A1 | 4/2017 | Matsuura | |
| 2018/0154053 A1 | 6/2018 | Shimada et al. | |
| 2018/0185562 A1 * | 7/2018 | Shimada | A61M 1/3635 |
| 2021/0316049 A1 | 10/2021 | Nakamura et al. | |

FOREIGN PATENT DOCUMENTS

| | | |
|---|---|---|
| CN | 103764251 | 4/2014 |
| CN | 105592870 | 5/2016 |
| CN | 104487105 | 12/2016 |
| JP | 4172631 | 10/2008 |
| JP | 2010-213820 | 9/2010 |
| JP | 5524340 | 6/2014 |
| JP | 2005-204781 | 8/2015 |
| JP | 2017-508553 | 3/2017 |
| TW | I446939 | 8/2014 |
| WO | 02/04045 | 1/2002 |
| WO | 2012/039400 | 3/2012 |
| WO | 2014/196651 | 12/2014 |
| WO | 2015/050216 | 4/2015 |
| WO | 2016/006574 | 1/2016 |
| WO | 2016/204289 | 12/2016 |
| WO | 2020/045592 | 3/2020 |

OTHER PUBLICATIONS

Supplementary European Search Report issued in for EP Application No. 20836146.9, dated Feb. 16, 2023.

Sueo Kawabata, Development of an Automatic Airpermeability Tester, Journal of the Textile Machinery Society of Japan, Apr. 1987, vol. 40, No. 6, pp. 41-49, p. 42 right column—pp. 43 left column and English language abstract.

International Search Report issued in International Pat. Appl. No. PCT/JP2020/026962, dated Sep. 8, 2020, along with an English translation thereof.

* cited by examiner

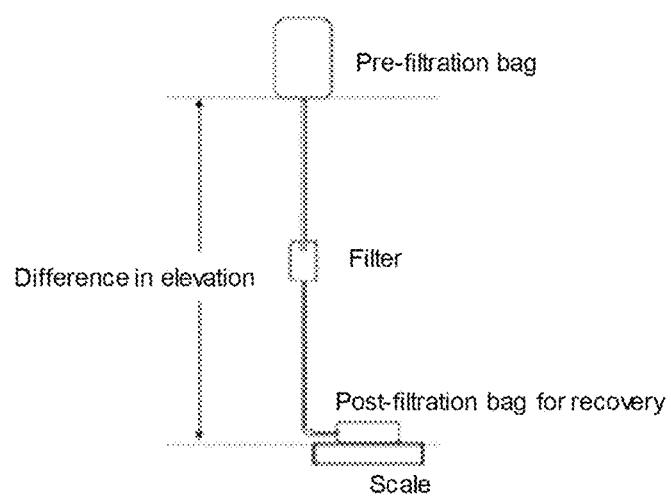

BLOOD PROCESSING FILTER

CROSS-REFERENCE TO RELATED APPLICATIONS

The present application is a U.S. National Stage of PCT/JP2020/026962 filed Jul. 10, 2020, and claims priority of Japanese Appl. No. 2019-129435 filed Jul. 11, 2019. The disclosure of Japanese Appl. No. 2019-129435 is expressly incorporated by reference herein in its entirety. PCT/JP2020/026962 published as WO2021006331 on Jan. 14, 2021.

TECHNICAL FIELD

The present invention relates to blood processing filters for removing unpreferable components such as aggregates and white blood cells from a liquid containing blood components or blood.

The present invention particularly relates to a blood processing filter for removing microaggregates and white blood cells that cause adverse side effects from whole blood preparations, red blood cell preparations, platelet preparations, and plasma preparations for blood transfusion.

BACKGROUND ART

Whole blood collected from donors is used as raw materials for blood component preparations such as red blood cell preparations, platelet preparations, and plasma preparations, however whole blood contains unpreferable components such as microaggregates and white blood cells that cause various blood transfusion adverse side effects. For this reason, unpreferable components are usually removed after blood collection or before a blood component preparation is used.

As methods for removing unpreferable components such as white blood cells from whole blood or blood component preparations, filter methods in which blood processing filters comprising a filter medium consisting of a fiber assembly such as a non-woven fabric or a pore structure having continuous pores have been widely used due to an easy operation and a low cost.

Conventionally, the blood processing filters that have been widely used had a filter medium consisting of a non-woven fabric or a porous body filled in a rigid container such as polycarbonate, however the container has a low gas permeability thus making it difficult to apply steam sterilization widely used as the sterilization step of a collected blood separation set, hence problematic. Further, in a closed system, there is a case where white blood cells are first removed from a whole blood preparation after blood collection and then the blood processing filter is detached to carry out a centrifugal operation to separate the components, and a case where whole blood is separated into a plurality of blood components by centrifugation and then white blood cells are removed, and in the latter case the blood processing filter is also centrifuged together with the collected blood separation set. During this operation, it is possible that a rigid container may damage a bag or a pipe, and itself may not withstand the stress during centrifugation, resulting in breakage.

As a method for solving these problems, "flexible blood processing filters" have been developed from the containers using a material excellent in flexibility and steam permeability that is the same as or similar to those that have been used for the bag for collected blood separation set.

Typically, when blood is processed using a blood processing filter, a bag containing a blood preparation to be processed and connected to the blood inlet side of the filter via a pipe is placed at a position about 20 cm to 100 cm higher than the filter to allow the blood preparation to pass through the filter by gravitation, and the blood preparation after filtration is held in a recovery bag connected to the blood outlet side of the filter via a pipe. During the filtration, a pressure loss is caused due to the resistance of a filter medium, whereby the space at the filter inlet side has a positive pressure. In the case of a filter formed of a flexible container, the container inflates like a balloon due to this positive pressure because the container is flexible and the filter medium tends to be pressed against the container at the outlet side.

A bag for storing blood after processed using the blood filter is typically placed at a position 50 cm to 100 cm lower than the filter, but the outlet side of the filter tends to have a negative pressure because the blood moves by the gravitation through a flow passage at the downstream side whereby the flexible container is likely to closely contact the filter medium.

That is, in the filters that use a flexible container, problems have been noted that the filter medium has a marked tendency to closely contact the container at the outlet side due to the double forces, thus preventing blood from flowing and failing to obtain a sufficient filtration flow rate and filtration performance.

The white blood cell removal filter performance is evaluated based on the white blood cell removal performance, •blood fluidity, and •blood recovery yield, and it is important to well demonstrate the balance thereof. However, the white blood cell removal performance and the blood fluidity particularly had an issue of being compatible due to the above reasons.

As a method for solving this problem, Patent Literature 1 discloses a technology of disposing a flow passage-securing sheet as a flow passage-securing member between a filter medium and the outlet side of a container, thus forming a continuous void that is not in close contact between the outlet side of the flexible container and the filter medium during filtration, thereby enabling the filtration flow rate and the white blood cell removal performance to be compatible.

Patent Literature 2 discloses a technology that a filter layer formed of a filter component element having specific properties is disposed in a specific thickness at the downmost stream position of a filter medium in contact with the outlet side of a container as a flow passage-securing member so that voids are formed in the filter layer even when the filter medium and the outlet side of the container are in close contact with each other during filtration, and blood flows through the filter layer in the direction perpendicular to the direction of filter medium thickness, thereby enabling a (high) filtration flow rate.

CITATION LIST

Patent Literature

Patent Literature 1: Japanese Patent No. 5524340
Patent Literature 2: Japanese Patent No. 4172631

SUMMARY OF INVENTION

Technical Problem

In Patent Literature 1, the flow passage-securing member itself does not have the white blood cell removal performance and thus the white blood cell removal performance cannot be maximized. Additionally, there was a problem of increasing a recovery yield loss of the liquid to be processed because blood remains in the flow passage and between a first sealed part and a second sealed part due to the flow passage-securing sheet.

In Patent Literature 2, the filter layer as a flow passage-securing member disposed at the downmost stream position of the filter medium in contact with the outlet side of the container can retain a flow passage inside even if it is compressed in sticking of the filter medium outlet side with the flexible container sheet at the outlet side, however when a filter layer (flow passage-securing member) amount is increased to enhance the flow, a recovery yield loss of the liquid to be processed increases, thereby posing a problem. When a filter medium amount is reduced, the white blood cell removal ability is decreased and all of the white blood cell removal performance, filtration flow rate, and blood recovery yield cannot be demonstrated simultaneously at high performances, thereby posing a problem.

These technologies have already been achieved to a level of being used as products, however the balance of these still needs to be improved.

The present invention aims to provide a blood processing filter excellent in all of the white blood cell removal performance, filtration time (filtration rate), and blood recovery.

Solution to Problem

The present inventors conducted extensive studies to solve the above problems and consequently found that when a blood processing filter in which a relatively dense filter layer, a relatively coarse filter layer, and a flow passage-securing member are disposed sequentially from upstream to downstream of the blood flow direction is used, the above problems can be solved, whereby the present invention has come to an accomplishment.

More specifically, the present invention relates to the followings.

[1]
A blood processing filter comprising:
a flexible container having an inlet and an outlet for blood,
a filter medium disposed between the inlet and the outlet in the flexible container, and
a flow passage-securing member disposed between the filter medium and the outlet in the flexible container,
wherein the filter medium comprises;
a filter layer X1 including a filter component unit A1, and
a filter layer Y including a filter component unit B,
wherein the filter layer X1 is disposed between the filter layer Y and the flow passage-securing member,
a ventilation resistance per thickness of the filter component unit A1 is 5.0 Pa·s/m$^2$ or more and less than 9.0 Pa·s/m$^2$,
a ventilation resistance per thickness of the filter component unit B is 9.0 Pa·s/m$^2$ or more,
a ventilation resistance of the filter layer X1 is 4.0 kPa·s/m or more and 20.0 kPa·s/m or less, and
a ventilation resistance of the filter medium is 55.0 kPa·s/m or more and less than 75.0 kPa·s/m.

[2]
The blood processing filter according to [1],
wherein the flow passage-securing member comprises a filter layer Z including a filter component unit P,
a ventilation resistance per thickness of the filter component unit P is less than 0.5 Pa·s/m$^2$, and
a ventilation resistance of the filter layer Z is 0.08 kPa·s/m or more and 0.16 kPa·s/m or less.

[3]
The blood processing filter according to [2], wherein a ventilation resistance of the filter layer Z is 0.08 kPa·s/m or more and 0.12 kPa·s/m or less.

[4]
The blood processing filter according to any one of [1] to [3],
wherein the filter medium further comprises a filter layer X2 including a filter component unit A2,
the filter layer X2 is disposed between the inlet and the filter layer Y,
a ventilation resistance per thickness of the filter component unit A2 is 5.0 Pa·s/m$^2$ or more and less than 9.0 Pa·s/m$^2$, and
a ventilation resistance of the filter layer X2 is 4.0 kPa·s/m or more.

Advantageous Effects of the Invention

According to the present invention, a blood processing filter excellent in all of the white blood cell removal performance, filtration time (filtration rate), and blood recovery can be provided.

BRIEF DESCRIPTION OF DRAWING

FIG. 1 is a schematic drawing of the experimental device used for the white blood cell removal performance test of the blood processing filters carried out in Examples.

DESCRIPTION OF EMBODIMENTS

Hereinafter, embodiments for carrying out the present invention (hereinafter, referred to as the present embodiment) will be described in detail. The present invention is not limited to the following embodiments and can be carried out in various modification within the spirit and scope thereof.

Hereinafter, unless otherwise specified, the term "blood" includes blood and blood component-containing liquids. Examples of the blood component-containing liquid include blood preparations. Examples of the blood preparation include whole blood preparations, red blood cell preparations, platelet preparations, and plasma preparations.

<Blood Processing Filter>

An embodiment of the present invention relates to a blood processing filter comprising:
a flexible container having an inlet and an outlet for blood,
a filter medium disposed between the inlet and the outlet in the flexible container, and
a flow passage-securing member disposed between the filter medium and the outlet in the flexible container,
wherein the filter medium comprises;
a filter layer X1 including a filter component unit A1, and
a filter layer Y including a filter component unit B,
wherein the filter layer X1 is disposed between the filter layer Y and the flow passage-securing member,
a ventilation resistance per thickness of the filter component unit A1 is 5.0 Pa·s/m$^2$ or more and less than 9.0 Pa·s/m$^2$,
a ventilation resistance per thickness of the filter component unit B is 9.0 Pa·s/m$^2$ or more,
a ventilation resistance of the filter layer X1 is 4.0 kPa·s/m or more and 20.0 kPa·s/m or less, and a ventilation resistance of the filter medium is 55.0 kPa·s/m or more and less than 75.0 kPa·s/m. The employment of such a structure enables the blood processing filter to demonstrate excellent performances in all of the white blood cell removal performance, filtration rate, and blood recovery.

In the blood processing filter according to the present embodiment, a filter layer Y, a filter layer X1, and a flow passage-securing member are disposed sequentially from an inlet toward an outlet of a flexible container. For this reason, blood to be processed enters the flexible container via the inlet, passes sequentially through the filter layer Y, the filter layer X1, and the flow passage-securing member and exits from the flexible container via the outlet.

The filter medium can include a further filter layer within the range of not affecting the effects of the present invention. For example, the filter medium preferably further contains a filter layer X2 including a filter component unit A2. Additionally, the filter layer X2 is preferably disposed between the inlet and the filter layer Y. In this embodiment, blood to be processed enters the flexible container via the inlet, passes sequentially through the filter layer X2, the filter layer Y, the filter layer X1, and the flow passage-securing member and exits from the flexible container via the outlet.

The shape of the blood processing filter of the present embodiment is not particularly limited and, for example, as the blood processing filter described in FIG. 14 of International Publication No. WO2015/050216, is preferably structured by a filter medium and a flexible container and has a sealed area in which a portion near the periphery of the filter medium is integrated with the flexible container all around, and further preferably has a first sealed area formed by integrating the portion near the periphery of the filter medium and the flexible container all around, a second sealed area formed by integrating the inlet side of the flexible container and the outlet side of the flexible container all around the outer periphery of the first sealed area, and a non-sealed area between the first sealed area and the second sealed area.

For the outer shape of the blood processing filter, various forms such as rectangular shapes, disc shapes, long disc shapes, and oval shapes can be employed but rectangular shapes are preferable to reduce a material loss during production, and thus the following embodiment will be described with an example of a rectangular shape.

[Flexible Container]

The flexible container is preferably a container molded from a sheet molded article or a cylindrical molded article which is made of a flexible resin. The flexible resin is preferably a flexible synthetic resin, and further preferably a flexible thermoplastic resin. The flexible resin, that has similar thermal property and electrical property to a filter medium, is favorable. Examples of the flexible resin include polyolefins such as soft polyvinyl chloride, polyurethane, an ethylene-vinyl acetate copolymer, polyethylene, and polypropylene, thermoplastic elastomers such as a hydrogenated product of a styrene-butadiene-styrene copolymer, and a styrene-isoprene-styrene copolymer or a hydrogenated product thereof, and a mixture of a thermoplastic elastomer and a softener such as polyolefin and ethylene-ethyl acrylate. The flexible resin is preferably a soft polyvinyl chloride, polyurethane, an ethylene-vinyl acetate copolymer, a polyolefin, and a thermoplastic elastomer having these as the main component, and further preferably a soft polyvinyl chloride and a polyolefin. Additionally, the flexible container is more preferably made from a material having a tensile modulus of elasticity of 7 N/mm$^2$ to 13 N/mm$^2$ and a thickness of 0.2 mm to 0.6 mm. The tensile modulus of elasticity is, when a tensile test is carried out, the ratio of tensile stress to strain corresponding thereto within the range in which the relationship of tensile stress (a per unit area load applied to a sample) and strain (modulus of elongation in the tensile direction of the sample) is in a linear relationship. In actuality, a tensile test of a flexible container material is carried out using an autograph (manufactured by Shimadzu Corporation, Model AG-5KNI) and a load cell (manufactured by Shimadzu Corporation, Model SLBL-500N) in accordance with JIS K 7113 (Testing Method for Tensile Properties of Plastics), and a gradient of the tangent at the deformation initiation point of the stress-strain curve is determined using a data processing software "TRAPEZIUM" (manufactured by Shimadzu Corporation), thereby to obtain a tensile modulus of elasticity.

[Filter Medium]

The filter medium is a member for processing blood, and more specifically a member for removing unpreferable components such as aggregates and white blood cells from blood. The filter medium comprises at least a filter layer X1 and a filter layer Y, preferably comprises a filter layer X1, a filter layer X2, and a filter layer Y, and is further preferably structured only by a filter layer X1, a filter layer X2, and a filter layer Y.

The filter layers include filter component units. When the number of filter component unit is 1, the component unit itself structures the filter layer. When the number of filter component unit is 2 or more, a plurality of filter component units are laminated and structure the filter layer. The number of filter component units is selected so that the filter layer has a predetermined ventilation resistance.

The filter layer X1 includes a filter component unit A1. The filter layer X1 can further include a filter component unit in addition to the filter component unit A1 but is preferably structured only by 1 or more filter component units A1.

The filter layer X2 includes a filter component unit A2. The filter layer X2 can further include a filter component unit in addition to the filter component unit A2 but is preferably structured only by 1 or more filter component units A2.

The filter layer Y includes a filter component unit B. The filter layer Y can further include a filter component unit in addition to the filter component unit B but is preferably structured only by 1 or more filter component units B.

The shape of the filter component unit is not particularly limited as long as it has pores capable of filtering blood and a predetermined ventilation resistance but preferably a fibrous medium such as a knitted fabric, a woven fabric and a non-woven fabric consisting of a natural fiber, a synthetic fiber, a glass fiber, or the like, porous membrane, and a sponge-like structure having three-dimensional network-like continuous pores.

The material for the filter component units is not particularly limited as long as it is unlikely to damage blood cells. Examples of the material for filter component units include an organic polymer material, an inorganic polymer material, and a metal. Of which, an organic polymer material is preferable for excellent workability such as cutting. Examples of the specific material for the filter component units include polyester, polyolefin, polyacrylonitrile, polyamide, polystyrene, polymethyl methacrylate, polyvinyl fluoride, polyurethane, polyvinyl alcohol, polyvinyl acetal, polysulfone, polyvinylidene fluoride, polytrifluorochlorovinyl, a vinylidene fluoride-tetrafluoroethylene copolymer, polyethersulfone, polyacrylate, a butadiene-acrylonitrile copolymer, a polyether-polyamide block copolymer, an ethylene-vinyl alcohol copolymer, cellulose, and cellulose acetate, with polyester and polyolefin being preferable, and polyester being particularly preferable.

The shape of the filter component unit A1, the filter component unit A2, and the filter component unit B can be same or different as long as each has a predetermined ventilation resistance. The shape of the filter component unit A1, filter component unit A2, and the filter component unit B is not particularly limited but preferably a fibrous medium, and further preferably a non-woven fabric.

The material of the filter component unit A1, the filter component unit A2, and the filter component unit B can be same or different as long as each has a predetermined ventilation resistance. The material of the filter component unit A1, filter component unit A2, and the filter component unit B is not particularly limited but preferably polyester.

The ventilation resistance per thickness of the filter component unit A1 is 5.0 Pa·s/m$^2$ or more and less than 9.0 Pa·s/m$^2$, preferably 5.0 Pa·s/m$^2$ or more and less than 8.0 Pa·s/m$^2$. When a ventilation resistance per thickness of the filter component unit A1 is within the above range, the flow passage in the filter component unit A1 is maintained even when the filter medium closely contacts the container at the outlet side during filtration, and thus the blood is not prevented from flowing whereby a sufficient filtration flow rate and filtration performance can be presumably obtained. In the present application, when a ventilation resistance per thickness of the filter component unit A1 is less than 5.0 Pa·s/m$^2$, a sufficient white blood cell removal performance cannot be obtained and the residual white blood cell count after filtration is more than 5.5 Log. When a ventilation resistance per thickness of the filter component unit A1 is 9.0 Pa·s/m$^2$ or more, a sufficient filtration flow rate cannot be obtained and the filtration time is 27 minutes or more.

The ventilation resistance per thickness of the filter component unit A2 is preferably 5.0 Pa·s/m$^2$ or more and less than 9.0 Pa·s/m$^2$, and more preferably 5.0 Pa·s/m$^2$ or more and less than 8.0 Pa·s/m$^2$. When a ventilation resistance per thickness of the filter component unit A2 is within the above range, excellent performances in the white blood cell removal performance and the filtration rate are demonstrated.

When a ventilation resistance per thickness of the filter component unit B is 9.0 Pa·s/m$^2$ or more, preferably 9.0 Pa·s/m$^2$ or more and less than 30.0 Pa·s/m$^2$, and more preferably 12.0 Pa·s/m$^2$ or more and less than 20.0 Pa·s/m$^2$. When a ventilation resistance per thickness of the filter component unit B is within the above range, excellent performance in the white blood cell removal performance is demonstrated. In the present application, when a ventilation resistance per thickness of the filter component unit B is less than 9.0 Pa·s/m$^2$, a sufficient white blood cell removal performance cannot be obtained and the residual white blood cell count after filtration is more than 5.5 Log.

The ventilation resistance of the filter layer X1 is 4.0 kPa·s/m or more and 20.0 kPa·s/m or less, and preferably 11.0 kPa·s/m or more and less than 16.0 kPa·s/m. When a ventilation resistance of the filter layer X1 is within the above range, excellent performances in all of the white blood cell removal performance, the filtration rate, and the blood recovery can be demonstrated. In the present application, when a ventilation resistance of the filter layer X1 is less than 4.0 kPa·s/m, a sufficient filtration flow rate cannot be obtained and the filtration time is 27 minutes or more due to the amount shortage of the filter component unit A1 even the design of the filter component unit A1 is appropriate.

When a ventilation resistance of the filter layer X1 is 20.0 kPa·s/m$^2$ or more, the white blood cell removal performance cannot be obtained and the residual white blood cell count after filtration is more than 5.5 Log, or a residual blood volume increases in the filter and a blood recovery yield decreases.

The ventilation resistance of the filter layer X2 is preferably 4.0 kPa·s/m or more, and more preferably 11.0 kPa·s/m or more and less than 16.0 kPa·s/m. When a ventilation resistance of the filter layer X2 is within the above range, excellent performances in the white blood cell removal performance and the filtration rate are demonstrated.

The ventilation resistance of the filter medium (the total of the ventilation resistances of all filter layers structuring the filter medium) is 55.0 kPa·s/m or more and less than 75.0 kPa·s/m, and preferably 60.0 kPa·s/m or more and less than 67.0 kPa·s/m. When a ventilation resistance of the filter medium is within the above range, a white blood cell removal performance can be demonstrated at a reasonable filtration rate expected as the blood processing filter. In the present application, when a ventilation resistance of the filter medium is less than 55.0 kPa·s/m, a filtration flow rate excessively increases and a sufficient white blood cell removal performance cannot be obtained, whereby a residual white blood cell count after filtration is more than 5.5 Log even when the filter component units A1, A2, and B, and the filter layers X1, X2, and Y are designed according to the present application. When a ventilation resistance of the filter medium is 75.0 kPa·s/m$^2$ or more, the filtration flow rate excessively decreases and the filtration time is 27 minutes or more even when the filter component units A1, A2, and B, and the filter layers X1, X2, and Y are designed according to the present application.

In the present description, the "ventilation resistance" (kPa·s/m) is the value measured in terms of differential pressure caused when a constant flow rate of air is passed through a sample (filter medium, filter layers, or filter component units). The ventilation resistance is measured by the method described in Examples.

The "ventilation resistance per thickness" (Pa·s/m$^2$) of the filter component unit is the value obtained by dividing a "ventilation resistance" (kPa·s/m) of a filter component unit by a "thickness" (mm) of the filter component unit. The "thickness" (mm) of a filter component unit is measured by the method described in Examples.

The method for controlling a ventilation resistance of the filter component unit is not particularly limited. For example, when the filter component unit is a non-woven fabric, the ventilation resistance can be adjusted by changing the fiber diameter and density of the non-woven fabric. At the same basis weight and density of the non-woven fabric, a smaller fiber diameter of the non-woven fabric is presumed to increase, for example, a specific surface area and thus a ventilation resistance. At the same fiber diameter of the non-woven fabric, a higher density is presumed to decrease, for example, a pore diameter and thus increase a ventilation resistance.

The fiber diameter and the density of a non-woven fabric can be adjusted based on the production conditions of the non-woven fabric. Examples of the production method of a non-woven fabric that has an easily adjustable fiber structure include a melt blown method. For example, a non-woven fabric having a predetermined ventilation resistance can be obtained by investigating spinning factors such as the resin viscosity, melting temperature, discharge quantity per pore, heated gas temperature, heated gas pressure, distance between a spinning spout and an accumulation net. A non-woven fabric having a reasonable ventilation resistance can also be produced by suitably changing production conditions based on the publicly known information (for example, "Fushokufu no Kiso to Oyo" ("Foundation and Application of non-woven fabric" in English), P. 119-127, published on Aug. 25, 1993, Japan Textile Machinery Association).

When a ventilation resistance and a thickness of the filter component units incorporated in the filter medium as a product are measured, the product is disassembled to take out the filter component units and a ventilation resistance and a thickness of each filter component unit are measured. However, a part at which a thickness is measured is the part at a distance of 1 cm or more from a welded part of the filter component units. Specifically, the filter medium is detached from the container near the periphery of the filtering surface and, when the filter medium is structured by a plurality of filter component units, these are peeled from each other to obtain each filter component unit. The filter component units in a product are separably integrated with other filter component units.

A high ventilation resistance means that it is difficult for air to pass through. For example, when the filter medium is structured by fibers, it suggests that the fibers are tangled in a dense or homogeneous state. For this reason, there are tendencies for blood being less likely to flow, blood cell clogging increasing, and thereby a processing speed decreasing.

On the other hand, a low ventilation resistance means that it is easy for air to pass through. For example, when the filter medium is structured by fibers, it suggests that the fibers are tangled in a coarse or non-homogeneous state. For this reason, there are tendencies for blood easily flowing but the number of contacts with white blood cells reducing, and thereby the white blood cell removal performance decreasing.

When filter component units having different ventilation resistances are used in combination at the specific disposition, the filtration rate and the white blood cell removal performance enhance, but the reason therefor is not clear. When a filter component unit having specific properties is disposed in a specific thickness at the upper stream side of a flow passage-securing member, a blood flow passage in the filter medium is not affected even when the outlet side of the flexible container closely contacts the filter medium during filtration, whereby it is estimated that the filtration flow rate is increased. Further, this presumably contributes to the enhancement of the effective filtration area, and as a result, it is estimated that the while blood cell removal ability is demonstrated even with the filter component unit having a coarse structure. However, the present invention is not limited to these estimated mechanisms.

In the present application, the design in which the filter layers X2, Y, and the flow passage-securing member are sequentially disposed fails to obtain a sufficient filtration flow rate and white blood cell removal performance, and the residual white blood cell count after filtration is more than 5.5 Log and the filtration time is 27 minutes or more.

[Flow Passage-Securing Member]

The flow passage-securing member refers to any member disposed between the filter medium and the outlet. The flow passage-securing member is not particularly limited as long as it can inhibit the flow of blood from being blocked by the close contact of the filter medium and the flexible container at the outlet side during filtration. Examples of the flow passage-securing member include a flow passage-securing sheet and a filter layer. Additionally, examples of the flow passage-securing member also include a tube disposed to prevent a filter medium from closely contacting a container therebetween (for example, European Patent No. 0526678 description), bumps and dents part formed on the inner surface of a container (Japanese Patent Laid-Open No. 11-216179), a screen made of knit fibers inserted between a filter medium and a container (International Publication No. WO95/017236), and a flexible frame sheet inserted between a filter medium and a container (International Publication No. WO2015/050216).

The flow passage-securing member forms a continuous void that is not in close contact between the outlet side of the flexible container and the filter medium during filtration and contributes to the enhancements of the filtration flow rate and the effective filtration area. In the present application, if the flow passage-securing member is not used, a sufficient filtration flow rate cannot be obtained and the filtration time is 27 minutes or more, and the effective filtration area decreases, whereby the white blood cell removal ability is 5.5 Log or more.

The flow passage-securing member preferably comprises a filter layer Z including a filter component unit P. The filter layer Z can include a further filter component unit in addition to the filter component unit P but is preferably structured only by 1 or more filter component units P.

Examples of the shape and material for the filter component unit P include those described in the above section "Filter medium." The shape of the filter component unit P is preferably fibrous medium, and further preferably a non-woven fabric. The material for the filter component unit P is preferably polyester.

The ventilation resistance per thickness of the filter component unit P is preferably less than $0.5$ $Pa·s/m^2$, and more preferably $0.1$ $Pa·s/m^2$ or more and less than $0.5$ $Pa·s/m^2$. When a ventilation resistance per thickness of the filter component unit P is within the above range, an excellent performance in the filtration flow rate is demonstrated.

The ventilation resistance of the filtration layer Z is preferably $0.08$ $kPa·s/m$ or more and $0.16$ $kPa·s/m$ or less, and more preferably $0.08$ $kPa·s/m$ or more and $0.12$ $kPa·s/m$ or less. When a ventilation resistance of the filter layer Z is within the above range, the risk of blood from remaining inside the blood processing filter can be reduced by reducing an amount of filter medium.

<Production Method of Blood Processing Filter>

The filter component units A1 and B that have been spun are laminated respectively to obtain the filter layers X1 and Y, and the filter layers Y and X1 as well as the flow passage-securing member are sequentially laminated. The filter component unit A2 is laminated as needed to obtain the filter layer X2, and the filter layer X2 is laminated in such a way as to be adjacent to the filter layer Y. This laminate is cut to a predetermined size using, for example, a knife, an ultrasonic cutter or a laser cutter to use as a filter medium.

The method for integrating the filter medium, the flow passage-securing member, and the flexible container is not particularly limited, and the integration can be achieved in the same manner as the conventional blood processing filters. For example, as described below, the integration can be achieved as in the blood processing filter (a flexible frame is used as the flow passage-securing member) described in FIGS. 1 to 3 of International Publication No. WO2015/050216. A flexible container having an inlet and a flexible container having an outlet are integrated by sealing like a belt along the periphery of a filter medium with the filter medium being interposed. This belt-like joined region along the periphery of the filter medium is an inner sealed part (a first sealed part). The inner sealed part is provided in such a way as not to include the peripheral edge of the filter medium. The inner side of the inner sealed part is the filtering part through which blood flows.

The peripheries of the flexible container having the inlet and the flexible container having the outlet are integrated by being sealed like a belt and, as a result, a rectangular-ring shaped outer sealed part (a second sealed part) is formed. The formation of the inner sealed part and the outer sealed part can be carried out utilizing high-frequency welding, but various joining techniques such as ultrasonic welding and heat welding can be used without limiting thereto.

The inlet and the outlet for blood can be formed by integrating with the flexible container in advance by a method such as injection molding, or by forming a hole or a slit in an extrusion-molded sheet film or a cylindrical film-molded article to which parts for the inlet and the outlet molded separately by injection molding or extrusion molding can be connected in a liquid-tight and communicated state by a known technique such as a joining agent, heat sealing, or high-frequency welding. The latter is more preferable from the reasons that a container is less likely to be deformed during steam sterilization and the production process is easy.

When the parts for the inlet and the outlet including tubular articles are installed in a sheet or cylindrical film in a liquid-tight manner, the material for the parts for the inlet and the outlet can be the same material as the sheet or cylindrical film, or can be a different material. In the case of a different material, the material is not particularly limited as long as the entrance and the exit can be respectively joined in a liquid-tight manner without any gaps with the sheet or cylindrical film and the handleability is not interfered. However, in the case of joining by heat sealing or high-frequency welding that is suitable for mass-production, the material preferably has similar thermal property and electrical property to the sheet or cylindrical film.

In the case of materials that have a relatively high permittivity such as soft polyvinyl chloride, preferable joining is achievable by high-frequency welding, whereas in the case of materials that have a low permittivity and a low melting point such as polyolefins, preferable joining is achievable by heat sealing.

EXAMPLES

Hereinafter, the present invention will be described in further details in reference to examples, but the present invention is not limited to the following examples.

The physical properties and performances of the blood processing filters were measured by the following methods.
(Measurement of Ventilation Resistance of the Filter Media, Filter Layers and Filter Component Units)

A sample (a filter medium, a filter layer, or a filter component unit) having a size of 5 cm×20 cm was placed on a vent (vent area $2\pi$ cm$^2$ ($\phi$1.414 cm)) of an air permeability tester (manufactured by KATO TECH CO., LTD., KES-F8-AP1), and a pressure loss (kPa·s/m) (a pressure difference between both sides divided by the sample) caused when air was ventilated at $8\pi$ cm$^3$/s for about 10 seconds was measured to define as a ventilation resistance.
(Measurement of a Thickness of the Filter Component Units)

A sample having a size of 5 cm×20 cm was cut out from the filter component elements and placed on a dial thickness gauge (model: G, maker: OZAKI MFG. CO., LTD.) to measure a thickness (mm) thereof.

(Measurement of a Ventilation Resistance Per Thickness of the Filter Component Units)

A ventilation resistance per thickness of the filter component unit was determined by dividing a ventilation resistance (kPa·s/m) of the filter component unit measured as the "(Measurement of ventilation resistance of the filter media, filter layers and filter component units)" by a thickness (mm) of the filter component unit measured as the "(Measurement of a thickness of the filter component unit)"
(White Blood Cell Removal Performance of Blood Processing Filters)

A red blood cell preparation prepared in accordance with the European Standard (the Guide to the Preparation, Use and Quality Assurance of Blood Components, 19th edition, (2017)) was used as a blood preparation, filtered and recovered using the blood processing filters of Examples and Comparative Examples with a natural difference in elevation of 110 cm thereby to obtain a blood preparation after filtration. The difference in elevation herein was defined as the distance from the lowest part of the bag containing the red blood cell preparation before filtration to the lowest part of the recovery bag for the red blood cell preparation after filtration (FIG. 1).

Subsequently, a white blood cell concentration in the blood preparation after filtration was measured using a white blood cell count measuring kit "LeucoCOUNT" manufactured by Becton, Dickinson and Company (BD) and a flow cytometer FACS Canto II manufactured by BD, and a residual white blood cell count (rWBC) after filtration was calculated in accordance with the following equation to use as the indicator for the white blood cell removal performance of the blood processing filters.

$$rWBC = \log \text{(white blood cell concentration in blood preparation after filtration} \times \text{amount of blood preparation after filtration)}$$

[Evaluation Criteria]
Good: Less than 5.0
Fair: 5.0 or more and less than 5.5
Poor: 5.5 or more
(Filtration Time)

In the "(White blood cell removal performance of blood processing filters)", the time (minute) required for a mass increase of the recovery bag for the red blood cell preparation after filtration to stop from the start of flowing the red blood cell preparation through the blood processing filter was defined as the filtration time (minute). The stop of a mass increase of the recovery bag refers to the point in time at which a mass of the recovery bag was measured by the minute from the start of filtration and a mass change of the recovery bag was 0.1 g or less. In the present examples, the filtration time was calculated by including the last 1 minute at which the stop of a mass increase was decided.
[Evaluation Criteria]
Good: less than 24 minutes
Fair: 24 minutes or more and less than 27 minutes
Poor: 27 minutes or more
(Blood Recovery Yield)

A blood loss volume (difference between a blood volume before filtration and a blood volume after filtration) was evaluated as the indicator of a blood recovery yield. From a weight of a bag set containing the red blood cell preparation before filtration and a red blood cell preservation solution, a weight of an empty bag set of the same form was subtracted to calculate a blood volume before filtration. After filtration, a circuit connecting the blood processing filter and the recovery bag was detached at a distance of 5 cm from the exit of the blood processing filter. From the thus obtained recovery bag weight, a weight of an empty recovery bag of the same form was subtracted to thereby calculate a blood volume after filtration.

[Evaluation Criteria]

Good: Less than 25 ml
Fair: 25 ml or more and less than 30 ml
Poor: 30 ml or more Examples 1 to 5

A non-woven fabric produced by the melt blown method was used as the filter component unit A1 and the filter component unit B. A non-woven fabric produced by the spunbond method was used as the filter component unit P.

A PBT non-woven fabric having a thickness: 0.42 (mm) and a ventilation resistance per thickness: 5.2 (Pa·s/m$^2$) as the filter component unit A1, a PBT non-woven fabric having a thickness: 0.41 (mm) and a ventilation resistance per thickness: 10.4 (Pa·s/m$^2$) as the filter component unit B, and a polyethylene terephthalate non-woven fabric having a thickness: 0.20 (mm) and a ventilation resistance per thickness: 0.20 (Pa·s/m$^2$) as the filter component unit P were superposed respectively by the number of sheets and the sequence shown in Table 1 to prepare laminates, which were cut to a size of 91 cm×74 cm using a laser cutter to make filter media.

This filter medium was interposed between 2 flexible polyvinyl chloride resin sheets having a port to be an inlet or an outlet for blood, and the filter medium and the peripheral part of the flexible sheets were integrated by welding using a high-frequency welding machine. The inner side of the welded part had a longitudinal dimension of 74 mm and a horizontal dimension of 57 mm, was the effective filtering part in rectangular with curved corners with an effective filtration area of 42 cm$^2$. The peripheral part of the flexible sheets was further integrated by welding to thereby make a blood processing filter. High-pressure steam sterilization was carried out on the blood processing filter at 115° C. for 59 minutes, and then the white blood cell removal performance test described above was carried out.

Examples 6 to 10, 15, 17

A blood processing filter was made by the same method as in Example 1 except that a PBT non-woven fabric having a thickness: 0.42 (mm) and a ventilation resistance per thickness: 7.3 (Pa·s/m$^2$) was used as the filter component unit A1, and the white blood cell removal performance test was carried out.

Examples 11 to 13

A blood processing filter was made by the same method as in Example 1 except that a PBT non-woven fabric having a thickness: 0.42 (mm) and a ventilation resistance per thickness: 8.7 (Pa·s/m$^2$) was used as the filter component unit A1, and the white blood cell removal performance test was carried out.

Example 14

A blood processing filter was made by the same method as in Example 6 except that a PBT non-woven fabric having a thickness: 0.41 (mm) and a ventilation resistance per thickness: 12.7 (Pa·s/m$^2$) was used as the filter component unit B, and the white blood cell removal performance test was carried out.

Examples 16, 18

A non-woven fabric produced by the melt blown method was used as the filter component unit A2.

A blood processing filter was made by the same method as in Example 14 except that a PBT non-woven fabric having a thickness: 0.42 (mm) and a ventilation resistance per thickness: 7.3 (Pa·s/m$^2$) was used as the filter component unit A2, and the white blood cell removal performance test was carried out.

Example 19

A non-woven fabric produced by the melt blown method was used as the filter component units A1 and A2 as well as the filter component unit B. For the flow passage-securing member, an inlet side frame sheet and an outlet side frame sheet made of a flexible polyvinyl chloride resin as described in International Publication No. WO2015/050216 were used.

A PBT non-woven fabric having a thickness: 0.42 (mm) and a ventilation resistance per thickness: 7.3 (Pa·s/m$^2$) was used as the filter component units A1 and A2. A PBT non-woven fabric having a thickness: 0.41 (mm) and a ventilation resistance per thickness: 12.7 (Pa·s/m$^2$) was used as the filter element B. The filter component units A1 and A2 as well as the filter component unit B were superposed respectively by the number of sheets and the sequence shown in Table 3 to prepare a laminate, which was cut to a size of 91 cm×74 cm using a laser cutter to make a filter medium.

This filter medium was interposed between the inlet side frame sheet and the outlet side frame sheet made of the flexible polyvinyl chloride resin, and the peripheral part of the filter medium was integrated by welding using a high-frequency welding machine. The inner side of the welded part had a longitudinal dimension of 74 mm and a horizontal dimension of 57 mm, was the effective filtering part in rectangular with curved corners with an effective filtration area of 42 cm$^2$. Further, the inlet side frame sheet and the outlet side frame sheet were interposed between 2 flexible polyvinyl chloride resin sheets having a port to be an inlet or an outlet for blood, and the peripheral parts of the flexible sheets were integrated by welding using a high-frequency welding machine to make a blood processing filter. High-pressure steam sterilization was carried out on the blood processing filter at 115° C. for 59 minutes, and then the various tests described above were carried out.

Comparative Examples 1, 2

Evaluations were made by the same method as in Examples 6 to 10 except that the number of sheets for each filter component unit structuring each filter layer was changed as shown in Table 4.

Comparative Examples 3, 10

Evaluations were made by the same method as in Example 14 except that the number of sheets for each filter component unit structuring each filter layer was changed as shown in Table 4 or Table 5.

Comparative Example 4

Evaluation was made by the same method as in Example 15 except that the number of sheets for each filter component unit structuring each filter layer was changed as shown in Table 4.

Comparative Example 5

Evaluation was made by the same method as in Example 16 except that the number of sheets for each filter component unit structuring each filter layer was changed as shown in Table 4.

Comparative Example 6

Evaluation was made by the same method as in Example 19 except that the number of sheets for each filter component unit structuring each filter layer was changed as shown in Table 4.

Comparative Example 7

A blood processing filter was made by the same method as in Example 4 except that a PBT non-woven fabric having a thickness: 0.42 (mm) and a ventilation resistance per thickness: 4.5 (Pa·s/m$^2$) was used as the filter component unit A1 as shown in Table 5, and the white blood cell removal performance test was carried out.

Comparative Example 8

A blood processing filter was made by the same method as in Example 1 except that a PBT non-woven fabric having a thickness: 0.42 (mm) and a ventilation resistance per thickness: 9.2 (Pa·s/m$^2$) was used as the filter component unit A1 as shown in Table 5, and the white blood cell removal performance test was carried out.

Comparative Examples 9, 11, 12

Evaluations were made by the same method as in Examples 6 to 10 except that a PBT non-woven fabric having a thickness: 0.41 (mm) and a ventilation resistance per thickness: 8.8 (Pa·s/m$^2$) was used as the filter component unit B, and the number of sheets for each filter component unit structuring each filter layer was changed as shown in Table 5.

Comparative Example 13

A non-woven fabric produced by the melt blown method was used as the filter component unit A2 as well as the filter component unit B.

A PBT non-woven fabric having a thickness: 0.42 (mm) and a ventilation resistance per thickness: 7.3 (Pa·s/m$^2$) was used as the filter component unit A2. A PBT non-woven fabric having a thickness: 0.41 (mm) and a ventilation resistance per thickness: 12.7 (Pa·s/m$^2$) was used as the filter element B. The filter component unit A2 as well as the filter component unit B were superposed by the number of sheets and the sequence as shown in Table 5 to prepare a laminate, which was cut to a size of 91 cm×74 cm using a laser cutter to make a filter medium.

Using this filter medium, blood processing filter was made by the same method as in Example 1, and the white blood cell removal performance test was carried out.

TABLE 1

| Filter layer | Filter component unit | Item | Unit | Example 1 | Example 2 | Example 3 | Example 4 | Example 5 | Example 6 | Example 7 |
|---|---|---|---|---|---|---|---|---|---|---|
| X2 | A2 | Thickness | mm | | | | | | | |
| | | Ventilation resistance per thickness | Pa·s/m$^2$ | | | | | | | |
| | | Number of component sheets for each layer | Number of sheets | | | | | | | |
| | | Ventilation resistance of each layer | kPa·s/m | | | | | | | |
| Y | B | Thickness | mm | 0.41 | 0.41 | 0.41 | 0.41 | 0.41 | 0.41 | 0.41 |
| | | Ventilation resistance per thickness | Pa·s/m$^2$ | 10.4 | 10.4 | 10.4 | 10.4 | 10.4 | 10.4 | 10.4 |
| | | Number of component sheets for each layer | Number of sheets | 12 | 12 | 12 | 12 | 12 | 12 | 12 |
| | | Ventilation resistance of each layer | kPa·s/m | 51.2 | 51.2 | 51.2 | 51.2 | 51.2 | 51.2 | 51.2 |
| X1 | A1 | Thickness | mm | 0.42 | 0.42 | 0.42 | 0.42 | 0.42 | 0.42 | 0.42 |
| | | Ventilation resistance per thickness | Pa·s/m$^2$ | 5.2 | 5.2 | 5.2 | 5.2 | 5.2 | 7.3 | 7.3 |
| | | Number of component sheets for each layer | Number of sheets | 2 | 3 | 4 | 5 | 6 | 2 | 3 |
| | | Ventilation resistance of each layer | kPa·s/m | 4.4 | 6.6 | 8.7 | 10.9 | 13.1 | 6.1 | 9.2 |
| Z | P | Thickness | mm | 0.20 | 0.20 | 0.20 | 0.20 | 0.20 | 0.20 | 0.20 |
| | | Ventilation resistance per thickness | Pa·s/m$^2$ | 0.2 | 0.2 | 0.2 | 0.2 | 0.2 | 0.2 | 0.2 |
| | | Number of component sheets for each layer | Number of sheets | 4 | 4 | 4 | 4 | 4 | 4 | 4 |
| | | Ventilation resistance of each layer | kPa·s/m | 0.16 | 0.16 | 0.16 | 0.16 | 0.16 | 0.16 | 0.16 |
| | | Flexible frame sheet | | Absent | Absent | Absent | Absent | Absent | Absent | Absent |
| | | Total number of sheets | Number of sheets | 18 | 19 | 20 | 21 | 22 | 18 | 19 |
| | | Total thickness | mm | 6.56 | 6.98 | 7.40 | 7.82 | 8.24 | 6.56 | 6.98 |
| | | Ventilation resistance of filter medium (X2 + Y + X1) | kPa·s/m | 55.7 | 57.9 | 60.1 | 62.2 | 64.4 | 57.5 | 60.5 |
| | Results | rWBC | Log | 5.1 | 4.9 | 4.8 | 4.8 | 4.7 | 5.2 | 4.9 |
| | | Filtration time | min | 24.4 | 22.1 | 21.5 | 22.8 | 23.8 | 25.1 | 23.5 |
| | | Blood loss volume | ml | 22.2 | 24.7 | 26.3 | 28.0 | 29.7 | 22.6 | 24.6 |

TABLE 2

| Filter layer | Filter component unit | Item | Unit | Example 8 | Example 9 | Example 10 | Example 11 | Example 12 | Example 13 | Example 14 |
|---|---|---|---|---|---|---|---|---|---|---|
| X2 | A2 | Thickness | mm | | | | | | | |
| | | Ventilation resistance per thickness | Pa · s/m$^2$ | | | | | | | |
| | | Number of component sheets for each layer | Number of sheets | | | | | | | |
| | | Ventilation resistance of each layer | kPa · s/m | | | | | | | |
| Y | B | Thickness | mm | 0.41 | 0.41 | 0.41 | 0.41 | 0.41 | 0.41 | 0.41 |
| | | Ventilation resistance per thickness | Pa · s/m$^2$ | 10.4 | 10.4 | 10.4 | 10.4 | 10.4 | 10.4 | 12.7 |
| | | Number of component sheets for each layer | Number of sheets | 12 | 12 | 12 | 12 | 12 | 12 | 12 |
| | | Ventilation resistance of each layer | kPa · s/m | 51.2 | 51.2 | 51.2 | 51.2 | 51.2 | 51.2 | 62.5 |
| X1 | A1 | Thickness | mm | 0.42 | 0.42 | 0.42 | 0.42 | 0.42 | 0.42 | 0.42 |
| | | Ventilation resistance per thickness | Pa · s/m$^2$ | 7.3 | 7.3 | 7.3 | 8.7 | 8.7 | 8.7 | 7.3 |
| | | Number of component sheets for each layer | Number of sheets | 4 | 5 | 6 | 2 | 4 | 5 | 2 |
| | | Ventilation resistance of each layer | kPa · s/m | 12.3 | 15.3 | 18.4 | 7.3 | 14.6 | 18.3 | 6.1 |
| Z | P | Thickness | mm | 0.20 | 0.20 | 0.20 | 0.20 | 0.20 | 0.20 | 0.20 |
| | | Ventilation resistance per thickness | Pa · s/m$^2$ | 0.2 | 0.2 | 0.2 | 0.2 | 0.2 | 0.2 | 0.2 |
| | | Number of component sheets for each layer | Number of sheets | 4 | 4 | 4 | 4 | 4 | 4 | 4 |
| | | Ventilation resistance of each layer | kPa · s/m | 0.16 | 0.16 | 0.16 | 0.16 | 0.16 | 0.16 | 0.16 |
| | | Flexible frame sheet | | Absent | Absent | Absent | Absent | Absent | Absent | Absent |
| | | Total number of sheets | Number of sheets | 20 | 21 | 22 | 18 | 20 | 22 | 18 |
| | | Total thickness | mm | 7.40 | 7.82 | 8.24 | 6.56 | 7.40 | 7.82 | 6.56 |
| | | Ventilation resistance of filter medium (X2 + Y + X1) | kPa · s/m | 63.6 | 66.7 | 69.7 | 58.6 | 65.9 | 69.6 | 68.8 |
| | Results | rWBC | Log | 4.7 | 4.6 | 4.6 | 5.4 | 5.1 | 5.0 | 5.4 |
| | | Filtration time | min | 23.0 | 23.2 | 24.8 | 26.5 | 25.0 | 25.5 | 26.5 |
| | | Blood loss volume | ml | 26.4 | 27.9 | 29.5 | 22.5 | 26.4 | 29.5 | 23.5 |

TABLE 3

| Filter layer | Filter component unit | Item | Unit | Example 15 | Example 16 | Example 17 | Example 18 | Example 19 |
|---|---|---|---|---|---|---|---|---|
| X2 | A2 | Thickness | mm | | 0.42 | | 0.42 | 0.42 |
| | | Ventilation resistance per thickness | Pa · s/m$^2$ | | 7.3 | | 7.3 | 7.3 |
| | | Number of component sheets for each layer | Number of sheets | | 4 | | 4 | 4 |
| | | Ventilation resistance of each layer | kPa · s/m | | 12.3 | | 12.3 | 12.3 |
| Y | B | Thickness | mm | 0.41 | 0.41 | 0.41 | 0.41 | 0.41 |
| | | Ventilation resistance per thickness | Pa · s/m$^2$ | 10.4 | 12.7 | 10.4 | 12.7 | 12.7 |
| | | Number of component sheets for each layer | Number of sheets | 9 | 7 | 12 | 7 | 7 |
| | | Ventilation resistance of each layer | kPa · s/m | 38.4 | 36.4 | 51.2 | 36.4 | 36.4 |
| X1 | A1 | Thickness | mm | 0.42 | 0.42 | 0.42 | 0.42 | 0.42 |
| | | Ventilation resistance per thickness | Pa · s/m$^2$ | 7.3 | 7.3 | 7.3 | 7.3 | 7.3 |
| | | Number of component sheets for each layer | Number of sheets | 6 | 4 | 4 | 4 | 4 |
| | | Ventilation resistance of each layer | kPa · s/m | 18.4 | 12.3 | 12.3 | 12.3 | 12.3 |
| Z | P | Thickness | mm | 0.20 | 0.20 | 0.20 | 0.20 | |
| | | Ventilation resistance per thickness | Pa · s/m$^2$ | 0.2 | 0.2 | 0.2 | 0.2 | |
| | | Number of component sheets for each layer | Number of sheets | 4 | 4 | 2 | 2 | |
| | | Ventilation resistance of each layer | kPa · s/m | 0.16 | 0.16 | 0.08 | 0.08 | |
| | | Flexible frame sheet | | Absent | Absent | Absent | Absent | Present |
| | | Total number of sheets | Number of sheets | 19 | 19 | 18 | 17 | 15 |
| | | Total thickness | mm | 7.01 | 7.03 | 7.00 | 6.63 | 6.23 |
| | | Ventilation resistance of filter medium (X2 + Y + X1) | kPa · s/m | 56.9 | 61.1 | 63.5 | 61.1 | 61.0 |
| | Results | rWBC | Log | 5.3 | 4.8 | 4.7 | 4.8 | 5.0 |
| | | Filtration time | min | 23.0 | 21.5 | 23.8 | 21.8 | 24.8 |
| | | Blood loss volume | ml | 25.0 | 25.5 | 24.6 | 23.6 | 28.3 |

TABLE 4

| Filter layer | Filter component unit | Item | Unit | Comparative Example 1 | Comparative Example 2 | Comparative Example 3 | Comparative Example 4 | Comparative Example 5 | Comparative Example 6 |
|---|---|---|---|---|---|---|---|---|---|
| X2 | A2 | Thickness | mm | | | | | | 0.42 |
| | | Ventilation resistance per thickness | Pa · s/m² | | | | | | 7.3 |
| | | Number of component sheets for each layer | Number of sheets | | | | | | 8 |
| | | Ventilation resistance of each layer | kPa · s/m | | | | | | 24.5 |
| Y | B | Thickness | mm | 0.41 | 0.41 | 0.41 | 0.41 | 0.41 | 0.41 |
| | | Ventilation resistance per thickness | Pa · s/m² | 10.4 | 10.4 | 12.7 | 10.4 | 12.7 | 12.7 |
| | | Number of component sheets for each layer | Number of sheets | 12 | 12 | 12 | 9 | 7 | 7 |
| | | Ventilation resistance of each layer | kPa · s/m | 51.2 | 51.2 | 62.5 | 38.4 | 36.4 | 36.4 |
| X1 | A1 | Thickness | mm | 0.42 | 0.42 | 0.42 | 0.42 | 0.42 | |
| | | Ventilation resistance per thickness | Pa · s/m² | 7.3 | 7.3 | 7.3 | 7.3 | 7.3 | |
| | | Number of component sheets for each layer | Number of sheets | 1 | 7 | 1 | 5 | 8 | |
| | | Ventilation resistance of each layer | kPa · s/m | 3.1 | 21.5 | 3.1 | 15.3 | 24.5 | |
| Z | P | Thickness | mm | 0.20 | 0.20 | 0.20 | 0.20 | 0.20 | |
| | | Ventilation resistance per thickness | Pa · s/m² | 0.2 | 0.2 | 0.2 | 0.2 | 0.2 | |
| | | Number of component sheets for each layer | Number of sheets | 4 | 4 | 4 | 4 | 4 | |
| | | Ventilation resistance of each layer | kPa · s/m | 0.16 | 0.16 | 0.16 | 0.16 | 0.16 | |
| | | Flexible frame sheet | | Absent | Absent | Absent | Absent | Absent | Present |
| | | Total number of sheets | Number of sheets | 17 | 23 | 17 | 18 | 19 | 15 |
| | | Total thickness | mm | 6.14 | 8.66 | 6.14 | 6.59 | 7.03 | 6.23 |
| | | Ventilation resistance of filter medium (X2 + Y + X1) | kPa · s/m | 54.4 | 72.8 | 65.7 | 53.9 | 61.1 | 61.0 |
| | Results | rWBC | Log | 5.5 | 4.6 | 5.7 | 5.5 | 5.5 | 5.5 |
| | | Filtration time | min | 27.5 | 26.0 | 29.0 | 22.0 | 25.0 | 28.1 |
| | | Blood loss volume | ml | 21.0 | 31.5 | 21.5 | 23.2 | 25.3 | 28.5 |

TABLE 5

| Filter layer | Filter component unit | Item | Unit | Comparative Example 7 | Comparative Example 8 | Comparative Example 9 | Comparative Example 10 | Comparative Example 11 | Comparative Example 12 | Comparative Example 13 |
|---|---|---|---|---|---|---|---|---|---|---|
| X2 | A2 | Thickness | mm | | | | | | | 0.42 |
| | | Ventilation resistance per thickness | Pa · s/m² | | | | | | | 7.3 |
| | | Number of component sheets for each layer | Number of sheets | | | | | | | 8 |
| | | Ventilation resistance of each layer | kPa · s/m | | | | | | | 24.5 |
| Y | B | Thickness | mm | 0.41 | 0.41 | 0.41 | 0.41 | 0.41 | 0.41 | 0.41 |
| | | Ventilation resistance per thickness | Pa · s/m² | 10.4 | 10.4 | 8.8 | 12.7 | 8.8 | 8.8 | 12.7 |
| | | Number of component sheets for each layer | Number of sheets | 12 | 12 | 14 | 13 | 11 | 15 | 7 |
| | | Ventilation resistance of each layer | kPa · s/m | 51.2 | 51.2 | 50.5 | 67.7 | 39.7 | 54.1 | 36.4 |
| X1 | A1 | Thickness | mm | 0.42 | 0.42 | 0.42 | 0.42 | 0.42 | 0.42 | |
| | | Ventilation resistance per thickness | Pa · s/m² | 4.5 | 9.2 | 7.3 | 7.3 | 7.3 | 7.3 | |
| | | Number of component sheets for each layer | Number of sheets | 5 | 2 | 3 | 3 | 7 | 1 | |
| | | Ventilation resistance of each layer | kPa · s/m | 9.5 | 7.7 | 9.2 | 9.2 | 21.5 | 3.1 | |
| Z | P | Thickness | mm | 0.20 | 0.20 | 0.20 | 0.20 | 0.20 | 0.20 | |
| | | Ventilation resistance per thickness | Pa · s/m² | 0.2 | 0.2 | 0.2 | 0.2 | 0.2 | 0.2 | |
| | | Number of component sheets for each layer | Number of sheets | 4 | 4 | 4 | 4 | 4 | 4 | |
| | | Ventilation resistance of each layer | kPa · s/m | 0.16 | 0.16 | 0.16 | 0.16 | 0.16 | 0.16 | |
| | | Flexible frame sheet | | Absent | Absent | Absent | Absent | Absent | Absent | Absent |
| | | Total number of sheets | Number of sheets | 21 | 18 | 21 | 20 | 22 | 20 | 15 |
| | | Total thickness | mm | 7.82 | 6.56 | 7.80 | 7.39 | 8.25 | 7.37 | 6.23 |
| | | Ventilation resistance of filter medium (X2 + Y + X1) | kPa · s/m | 60.8 | 59.1 | 59.9 | 77.0 | 61.3 | 57.3 | 61.0 |
| | Results | rWBC | Log | 5.6 | 5.3 | 5.5 | 4.4 | 5.5 | 5.7 | 5.5 |
| | | Filtration time | min | 23.4 | 28.2 | 23.0 | 32.0 | 23.9 | 26.0 | 35.0 |
| | | Blood loss volume | ml | 29.0 | 24.0 | 29.2 | 28.0 | 30.5 | 28.1 | 24.0 |

INDUSTRIAL APPLICABILITY

The blood processing filters of the present invention can be used as the blood processing filter for removing unpreferable components such as aggregates and white blood cells from a liquid containing blood components or blood.

Particularly, the blood processing filters of the present invention can be preferably used as a disposable blood processing filter used for the purpose of removing microaggregates and white blood cells that cause adverse side effects from whole blood preparations, red blood cell preparations, platelet preparations, and plasma preparations for blood transfusion.

The invention claimed is:

1. A blood processing filter comprising:

a flexible container having an inlet and an outlet for blood, a filter medium disposed between the inlet and the outlet in the flexible container, wherein the filter medium is configured to allow the blood to pass therethrough so as to process the blood by filtration, and a flow passage-securing member disposed between the filter medium and the outlet in the flexible container, wherein the filter medium comprises;

a filter layer X1 including a filter component unit A1, and a filter layer Y including a filter component unit B, wherein the filter layer X1 is disposed between the filter layer Y and the flow passage-securing member, a ventilation resistance per thickness of the filter component unit A1 is 5.0 Pa·s/m$^2$ or more and less than 9.0 Pa·s/m$^2$, a ventilation resistance per thickness of the filter component unit B is 9.0 Pa·s/m$^2$ or more, a ventilation resistance of the filter layer X1 is 4.0 kPa·s/m or more and 20.0 kPa·s/m or less, and a ventilation resistance of the filter medium is 55.0 kPa·s/m or more and less than 75.0 kPa·s/m.

2. The blood processing filter according to claim 1, wherein the flow passage-securing member comprises a filter layer Z including a filter component unit P, a ventilation resistance per thickness of the filter component unit P is less than 0.5 Pa·s/m$^2$, and a ventilation resistance of the filter layer Z is 0.08 kPa·s/m or more and 0.16 kPa·s/m or less.

3. The blood processing filter according to claim 2, wherein the ventilation resistance of the filter layer Z is 0.08 kPa·s/m or more and 0.12 kPa·s/m or less.

4. The blood processing filter according to claim 1, wherein the filter medium further comprises a filter layer X2 including a filter component unit A2, the filter layer X2 is disposed between the inlet and the filter layer Y, a ventilation resistance per thickness of the filter component unit A2 is 5.0 Pa·s/m$^2$ or more and less than 9.0 Pa·s/m$^2$, and a ventilation resistance of the filter layer X2 is 4.0 kPa·s/m or more.

* * * * *